United States Patent [19]

Nieman et al.

[11] Patent Number: 5,977,091

[45] Date of Patent: Nov. 2, 1999

[54] METHOD OF PREVENTING ACUTE LUNG INJURY

[75] Inventors: Gary Nieman; Anthony Picone, both of Manlius; Charles Lutz, Syracuse; David Carney, Dewitt; Louis Gatto, Cortland; Lorne M. Golub, Smithtown; Sanford Simon, Stony Brook; Nungavarm S. Ramamurthy, Smithtown, all of N.Y.

[73] Assignee: The Research Foundation of State University of New York, Albany, N.Y.

[21] Appl. No.: 09/157,727

[22] Filed: Sep. 21, 1998

[51] Int. Cl.[6] .................................................. A61K 31/65
[52] U.S. Cl. .............................................. 514/152
[58] Field of Search ............................... 514/152

[56] References Cited

U.S. PATENT DOCUMENTS

| 5,523,297 | 6/1996 | Pruzanski et al. | 514/152 |
| 5,532,227 | 7/1996 | Golub et al. | 514/152 |
| 5,773,430 | 6/1998 | Simon et al. | 514/152 |
| 5,837,696 | 11/1998 | Golub et al. | 514/152 |

OTHER PUBLICATIONS

Derwent Abstract of WO95/03057 Arai, et al., Feb. 1995.

*Primary Examiner*—Raymond Henley, III
*Attorney, Agent, or Firm*—Hoffmann & Baron, LLP

[57] ABSTRACT

The invention discloses a novel method for preventing acute lung injury in a mammal following trauma. The method includes treating the mammal with an effective amount of a tetracycline prior to intrapulmonary accumulation of neutrophils.

6 Claims, 5 Drawing Sheets

Figure 1. Time course for all groups. Following surgical preparation animals were exposed to either cardiopulmonary bypass (CPB) or Sham CPB (surgical preparation without bypass) for 60 minutes. The time necessary to wean from CPB, reverse heparin, and obtain baseline hemodynamics was approximately 30 minutes. Next groups were exposed to infusion of either *E. coli* lipopolysaccharide (LPS) or Sham LPS (infusion of saline vehicle only) over 60 minutes. Animals were euthanized at 270 minutes (3 hours after onset of LPS/Sham LPS).

Figure 2. Change in arterial PO$_2$ over time. Data expressed as mean±SEM. *=p<0.05 vs Baseline; †=p<0.05 vs All Groups Figure 3. Change in Ventilatory Efficiency Ratio over time. Data expressed as mean±SEM.

*=p<0.05 vs Baseline; ¶=p<0.05 vs All Groups on CPB; †=p<0.05 vs All Groups.

Figure 4. Change in pulmonary venous admixture over time. Data expressed as mean±SEM.

*=p<0.05 vs Baseline; †=p<0.05 vs All Groups.

Figure 5. Elastase and total MMP (gelatinase) activity. Elastase activity expressed as nanomolar concentration of elastase substrate (MeOSuc-Ala+Ala+Pro+Val-p-nitroanilide) degraded per milligram of protein per hour. Amidolytic activity was measured from bronchioalveolar lavage fluids obtained at necropsy. Total MMP gelatinase activity expressed as nanograms of gelatin degraded per milligram of protein per hour. Bronchioalveolar lavage fluid obtained at necropsy was treated with APMA and SBTI to activate MMPs and inhibit serine proteinases. Data expressed as mean±SEM. *=$p<0.05$ vs All Groups.

METHOD OF PREVENTING ACUTE LUNG INJURY

Acute respiratory distress syndrome (ARDS) is a critical illness characterized by acute lung injury leading to permeability pulmonary edema and respiratory failure. The clinical scenarios that place patients at risk for ARDS are as diverse as trauma, hemorrhage or sepsis. Despite significant advances in critical care management, mortality from ARDS remains over 40%. Each year over 100,000 people die in the United States from complications of ARDS.

Circulating inflammatory cells, particularly neutrophils, play a major role in the onset and progression of acute lung injury in both humans and experimental animal models. Several investigators have demonstrated extensive intrapulmonary accumulation of neutrophils in cases of ARDS. Once activated, these neutrophils release proteases, including matrix metalloproteinases, and other mediators of lung injury.

In cases of sepsis-induced ARDS, neutrophils that have accumulated in the lungs are activated by endotoxins. Accordingly, one approach to treat such cases is the administration of an endotoxin neutralizer. Japanese patent application No. WO95/03057 of Chugai Pharmaceuticals discloses an endotoxin neutralizer which contains, as an active ingredient, a tetracycline or its derivative. The tetracycline, or its derivative, need not have antibacterial activity. This endotoxin neutralizer is said to be used therapeutically or preventively for conditions caused by endotoxins.

Sakamaki et al., Effect of a Specific Neutrophil Elastase Inhibitor, ONO-5046, on Endotoxin-Induced Acute Lung Injury, Am. J. Respir. Crit. Care Med. 153, 391–397 (1996), discloses an investigation of the effects of a neutrophil-elastase inhibitor, N-[2-[4-(2,2-dimethylpropionyloxy)-phenylsulfonylamino] benzoyl] aminoacetic acid (ONO-5046), on parameters of acute lung injury. The authors found that acute lung injury may be attenuated by ONO-5046.

According to Sakamaki et al., three of the symptoms of ARDS observed in clinical settings are accumulation of neutrophils in lung tissue, transient depletion of neutrophil counts in peripheral blood and an increase of neutrophil counts in bronchoalveolar lavage fluid. Of these three symptoms, ONO-5046 was observed to reverse only the increase of the neutrophil counts in the bronchoalveolar lavage fluid. The effects were said to be due to the ability of ONO-5046 to inhibit elastase.

Searles et al., Antiprotease Reduces Acute Lung Injury in a Porcine Model of Post Pump Syndrome, AmSECT, 35th International Conference, (Abstract), (1997) discloses a neutrophil elastase inhibitor for the treatment of post pump syndrome. Post pump syndrome is acute respiratory distress syndrome which follows cardiopulmonary bypass. The neutrophil elastase inhibitor used in this experiment is dedimethylamino-6-demethyl-6-deoxytetracycline, a nonantimicrobial tetracycline derivative.

In the experiment described by Searles et al., post-pump syndrome was induced in two stages. First, cardiopulmonary bypass caused neutrophils to be sequestered in the pulmonary vasculature. Next, administration of low dose endotoxin, (lipopolysaccharide) activated the sequestered neutrophils to secrete proteases. When COL-3 was administered simultaneously with lipopolysaccharide, lung injury was avoided. Searles et al. reported that lung injury was avoided with the administration of COL-3 because the activity of neutrophil elastase and gelatinase was ameliorated.

An article by Shapiro et al. (Mice Lacking Neutrophil Elastase Reveal Impaired Host Defense Against Gram Negative Bacteria Sepsis, Nature Medicine 4, 615 (May 1998)) discloses an experiment demonstrating that neutrophil elastase (NE) does not have an effect on neutrophil migration. In their experiment, strains of mice were genetically altered to be deficient in NE. The mice were found by Shapiro et al. to have increased susceptibility to bacterial infection. The inability to efficiently clear bacteria from sites of infection was found not to be due to the impairment of neutrophils to egress from the bloodstream and migrate to sites of infection. Neutrophil migration to sites of infection in mice deficient in NE was as efficient as neutrophil migration in mice not deficient in NE.

Neutrophil mobilization to secondarily infected tissues was also found by Shapiro et al. to be equal in both normal and NE deficient mice. (See page 615, column 2, the last full paragraph.) The secondary tissue examined included lung tissue. (See FIG. 2(d).)

The increase in the susceptibility to gram negative bacteria, reported by Shapiro et al., was found to be due to impaired intracellular killing capacity of the NE deficient mice, not due to impaired neutrophil migration. Thus, the Shapiro et al. study illustrates that the presence of NE is not necessary for neutrophils to accumulate at an infection site, including the lungs.

The prior art treatments for ARDS discussed above are inadequate. The ideal treatment for ARDS (i) would prevent neutrophil accumulation in the lung, and (ii) would be independent of how neutrophils are activated and recruited into the lungs.

For example, the Chugai application is limited to treating ARDS acquired from bacterial infection by neutralizing endotoxin. Endotoxin may play an important role in the pathogenesis of some forms of ARDS by priming and activating the neutrophils to secrete elastase. However, approximately half of the total ARDS population acquire the pathology by triggers other than endotoxins, such as trauma. (CHEST 110, 273S–277S (1996); Clinical Infectious Diseases 14, 1213–1228 (1992)). An endotoxin neutralizer would be ineffective in the treatment of such cases.

The Sakamaki et al. article also discloses an NE inhibitor as a treatment for ARDS. Since the authors teach that the NE inhibitor, ONO-5046, does not inhibit chemotaxis of the neutrophils, there is no suggestion that ONO-5046 should be administered prior to intrapulmonary accumulation of neutrophils. ONO-5046 is suggested to be administered only after the onset of NE activity.

Treating ARDS by inhibiting NE, as suggested by Searles et al. and Sakamaki et al., is important but a bit late since some intrapulmonary damage due to the accumulation of neutrophils in the lung may have already occurred. A more effective protocol for potential victims of ARDS would be to begin treatment prior to the onset of any elastase activity.

The objective of this invention is to treat trauma patients, who are potential victims of ARDS, prior to intrapulmonary accumulation of neutrophils that give rise to pathologically elevated levels of elastase and MMPs.

SUMMARY

These and other objectives, as would be apparent to those ordinarily skilled in the art, have been achieved by providing a novel method for preventing acute lung injury in a mammal following trauma. The method comprises treating the mammal with an effective amount of a tetracycline prior to intrapulmonary accumulation of neutrophils.

DETAILED DESCRIPTION

The invention relates to preventing acute lung injury. Acute lung injury is damage to lung tissue caused by neutrophils which have infiltrated into the lungs. The neutrophils secrete mediators of lung injury, such as proteases and oxidants. These mediators lead to a massive loss in the selective permeability of both the capillary endothelium and alveolar epithelium. Examples of critical illnesses characterized by acute lung injury are acute respiratory distress syndrome (ARDS) and post-pump syndrome (PPS).

One cause of the infiltration of neutrophils into the lungs is trauma. Trauma, for the purposes of the instant invention, could be any injury to living tissue caused by an extrinsic agent or event. This would include, for example, any crush injury, contact with a hard surface, or cutting or other damage to the endothelium, epithelium, or internal organs. Such trauma could result, for example, from surgery, accident, etc.

A mammal which can benefit from the treatment prescribed by the instant invention could be any mammal. Categories of mammals include humans, farm mammals, domestic mammals, laboratory mammals, etc. Some examples of farm mammals include cows, pigs, horses, goats, etc. Some examples of domestic mammals include dogs, cats, etc. Some examples of laboratory mammals include rats, mice, rabbits, guinea pigs, etc.

The method of the invention involves the administration of a tetracycline compound. Tetracyclines are a class of compounds which are particularly well known for their early and spectacular success as antibiotics. Such compounds as tetracycline, sporocycline, etc., are broad spectrum antibiotics, having utility against a wide variety of bacteria and other microbes. The parent compound, tetracycline, has the following general structure:

The numbering system of the multiple ring nucleus is as follows:

Tetracycline, as well as the 5-OH (oxytetracycline, e.g. terramycin™) and 7-Cl (chlorotetracycline, e.g., aureomycin™) derivatives, exist in nature, and are all well known antibiotics. Natural tetracyclines may be modified without losing their antibiotic properties, although certain elements of the structure must be retained to do so. Semi-synthetic tetracyclines include, for example, doxycycline, minocycline and methacycline.

The use of tetracycline antibiotics, while generally effective for treating infection, can lead to undesirable side effects. For example, the long-term administration of antibiotic tetracyclines can reduce or eliminate healthy flora, such as intestinal flora, and can lead to the production of antibiotic resistant organisms or the overgrowth of yeast and fungi. These significant disadvantages typically preclude treatment regimens requiring chronic administration of these compounds.

A class of compounds has been defined which are structurally related to the antibiotic tetracyclines, but which have had their antibiotic activity substantially or completely eliminated by chemical modification. Substantial elimination of antibiotic activity occurs when the antibiotic activity is ten times less than that of tetracycline, and preferably five times less than that of tetracycline.

The modifications that may and may not be made to the basic tetracycline structure were reviewed by Mitscher, L. A., The Chemistry of the Tetracycline Antibiotics, Marcel Dekker, New York (1978), Ch. 6. According to Mitscher, the modification at positions 5–9 of the tetracycline ring system can be made without causing the complete loss of antibiotic properties. However, changes to the basic structure of the ring system, or replacement of substituents at positions 1–4 or 10–12, generally lead to synthetic tetracyclines with substantially less, or essentially no, antibacterial activity.

The preferred tetracycline compound is modified chemically to reduce or eliminate its antimicrobial properties. Chemically modified nonantimicrobial tetracyclines (CMT's) include, for example, 4-de(dimethylamino) tetracycline (CMT-1), tetracyclinonitrile (CMT-2), 6-demethyl-6-deoxy-4-de(dimethylamino)tetracycline (CMT-3), 7-chloro-4-de(dimethylamino)tetracycline (CMT-4), tetracycline pyrazole (CMT-5), 4-hydroxy-4-de (dimethylamino)tetracycline (CMT-6), 4-de (dimethylamino-12α-deoxytetracycline (CMT-7), 6-deoxy-5α-hydroxy-4-de(dimethylamino)tetracycline (CMT-8), 4-de(dimethylamino)-12α-deoxyanhydrotetracycline (CMT-9), 4-de(dimethylamino)minocycline (CMT-10).

The chemically modified tetracyclines can be made by methods known in the art. See, for example, Mitscher, L. A., The Chemistry of the Tetracycline Antibiotics, Marcel Dekker, New York (1978), Ch. 6, and U.S. Pat. Nos. 4,704,383 and 5,532,227.

The amount of the tetracycline compound administered is any amount effective for reducing or inhibiting neutrophil accumulation in the lungs. Nonantimicrobial tetracycline derivatives can be used at higher levels than antimicrobial tetracyclines, while avoiding certain disadvantages, such as the indiscriminate killing of beneficial microbes which often accompanies the use of antimicrobial or antibacterial amounts of such compounds.

The maximal dosage for a subject is the highest dosage which does not cause undesirable or intolerable side effects. For example, the tetracycline compound can be administered in an amount of from about 0.1 mg/kg/day to about 24 mg/kg/day, and preferably from about 2 mg/kg/day to about 18 mg/kg/day. For the purpose of the present invention, side effects include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes without limitation dosages which are effective to achieve the described phenomena.

The preferred pharmaceutical composition for use in the method of the invention comprises a combination of the tetracycline compound in a suitable pharmaceutical vehicle as understood by practitioners in the art.

For the pharmaceutical purposes described above, the tetracycline of the invention can be formulated per se in pharmaceutical preparations optionally with known pharmaceutically acceptable adjuvants or carriers. These preparations can be made according to conventional chemical methods and can be administered internally, e.g., orally by tablet or liquid, or by suppository; parenterally, e.g., intravenously, intramuscularly or subcutaneously, as injectable solutions or suspensions; topically or in the form of a spray or aerosol of droplets within the respirable range for inhalation into the lungs and airways. Such aerosols may include vehicles such as pulmonary surfactant preparations which may contribute additional therapeutic efficacy. Time-release or controlled-delivery administration may be employed.

It will be appreciated that the actual preferred amounts of active compound in a specified case will vary according to the particular compositions formulated, the mode of application, and the particular sites and subject being treated. Dosages will be determined using conventional considerations, e.g., by customary comparison of the differential activities of the formulations and of a known agent, e.g., by means of an appropriate conventional pharmacological protocol.

For the purposes of the instant specification, an acute lung injury is considered prevented if the tetracycline leads to a significant inhibition of the injury. As a result of the treatment, a patient would not sustain any injury, or would sustain significantly less injury, than without the treatment. In other words, the patient would have an improved medical condition as a result of the treatment.

The method of the invention involves administration of the tetracyclines any time prior to significant intrapulmonary accumulation of neutrophils in the lung. Thus, the upper limit of this time period is determined by the significant accumulation of neutrophils in the lung. Preferably administration of the tetracyclines occurs within 48 hours after trauma, more preferably within 24 hours after trauma, most preferably within 12 hours after trauma and optimally within 6 hours after trauma. Significant intrapulmonary neutrophil accumulation in the lung can be inferred from systemic neutropenia. A white cell count of approximately 4,000 or less white blood cells per microliter of blood is indicative of a neutropenia in which significant neutrophil accumulation in the lung area has occurred.

EXAMPLE

Surgical Preparation

Healthy Yorkshire hybrid pigs (15–20 kg) were preanesthetized with ketamine (30 mg/kg, IM) and xylazine (2 mg/kg, IM) and then pretreated with atropine (0.05 mg/kg, IM) 10–15 minutes prior to intubation. Anesthesia was induced with I.V. sodium pentobarbital (50 mg/ml) and a tracheostomy was established. Animals were ventilated with an anesthesia ventilator (Narkomed Drager AV). Continuous anesthesia with sodium pentobarbital (6 mg/kg/hr) was delivered via a Harvard infusion pump (Model 907), while bolus infusion of pancuronium bromide was given to maintain paralysis.

A right carotid artery cutdown was performed and 2 mm ID polyethylene tubing was used to measure systemic artery pressure. A 7.5 French triple lumen catheter was placed into the adjacent internal jugular vein for maintenance IV fluids, anesthetic agents, drug, and infusion of $E.\ coli$ lipopolysaccharide (LPS). A left femoral artery cutdown was established with 2 mm ID polyethylene tubing for analysis of blood gases (Radiometer Inc., Model ABL5) and blood oxygen contents (Radiometer Inc., Model OSM3). A 7 French flow-directed Swan-Ganz thermodilution catheter was passed through the left femoral vein into the pulmonary artery for tracing analysis to assess pulmonary artery pressure (PAP) and pulmonary artery occlusion pressure (PAOP). Pressures were measured using transducers (Argon™ Model 049-992-000A) leveled with the right atrium and recorded on a Hewlett Packard Monitor/Terminal (78534C) with a Hemodynamic Module (78551D). Additionally the Swan-Ganz catheter was used to obtain samples for mixed venous $O_2$ saturation and content. Finally, thermodilution function was used to obtain cardiac output (Baxter, Explorer™). Cardiac output measurements were made in duplicate at end-expiration. Electrocardiographic (ECG) monitoring was performed with a ECGlPressure module. End-expired $PCO_2$ was measured with a Hewlett Packard $CO_2/FiO_2$ Module (78556A) connected to the expiratory line of the ventilator airway adaptor (14365A) and capnometer sensor (14360A).

A cystotomy was performed through a low midline incision and a Foley catheter and temperature probe were placed into the bladder. Initial ventilator settings were $FiO_2=50\%$, Tidal Volume 12 cc/kg, and Rate=10. Adjustments were made in the respiratory rate to obtain a baseline $PaCO_2=$ 45–55 mmHg. The lung was sighed every 30 minutes by manual delivery of 1.5× the set tidal volume. Preliminary experiments in our laboratory have shown that induction of ARDS causes fatal elevation of arterial $PCO_2$. Therefore, base excesses (BE) below −3 mEq/L were corrected with intravenous sodium bicarbonate and adjustments were made in ventilatory rate to maintain $PaCO_2$ within normal range (4–45 mmHg). Heating pads and warmed I.V. fluids were utilized to maintain a core temperature between 34–38° C.

All groups received Lactated Ringers solution (25 ml/kg/hr) in addition to bolus infusion of Dextran 70 to maintain cardiac output (CO) within 10% of baseline.

Cardiopulmonary Bypass

After a baseline activated clotting time (ACT) was obtained (Hemochron 401 whole blood coagulation instrument, International Technidyne Corp.), all animals to be placed on cardiopulmonary bypass (CPB) were fully anticoagulated with heparin (300 U/kg). With verification of adequate anticoagulation (ACT>480 seconds), a surgical cutdown was performed to facilitate placement of an arterial cannula (USCI 14 F arterial catheter) into the right femoral artery, and a venous cannula (Medtronic® 18 french percutaneous femoral arterial catheter) into the right femoral vein which was advanced into the right atrium. The cardiopulmonary bypass circuit included Cobe® oxygenators (Cobe Duo flat plate membrane), tubing pack, an arterial filter (40 μm), and a Sarns® roller pump. The pump prime solution consisted of lactated Ringers (1500 ml), mannitol (5 gm), sodium bicarbonate (35 meq), and porcine lung heparin (300 Units/kg).

Nonpulsatile CPB was initiated at a flow rate of 120 mL/kg. Mean arterial blood pressure was maintained (30–60 mmHg) by adjusting blood flow rate. Oxygen and air flow to the oxygenator were titrated to maintain physiologic blood gases (pH 7.35–7.45, $PCO_2$ 35–40 mmHg, and $PO_2$ 150–300 mmHg). During CPB the integrated warming coils in the blood reservoir were used to decrease body temperature to 28° C. over a period of 10–15 minutes. Body temperature was returned to normal over 20 minutes before terminating CPB. Thirty minutes prior to termination of CPB, intravenous infusion of isoproterenol (1 mg/kg) was initiated. Since pigs were not on full bypass support, isoproterenol facilitated effective ejection volume to eliminate cardiac distension and prevent ischemia. Isoproterenol was weaned to maintain systemic arterial pressure within 10% of baseline values. Five minutes before discontinuation of CPB, calcium chloride (500 mg) and magnesium sulfide (1 gm) were given to avoid dysrhythmias associated with electrolyte imbalance. Within 30 minutes animals had returned to a baseline status defined as: 1) all blood within the oxygenator was transfused back into the animal, 2) heparin was reversed with protamine (1.3 mg/100 Units heparin), and 3) pulmonary pressures, systemic pressure, and cardiac output were all within 10% of baseline without assistance from inotropic agents. Animals not randomized to an arm which was exposed to CPB received Sham CPB (surgical preparation without anticoagulation or bypass).

Endotoxin Infusion

Pigs receiving LPS were infused with 1 μg/kg of *E. Coli* lipopolysaccharide (LPS; SIGMA 111: B4) mixed in 500 ml of saline and delivered over one hour via a volumetric infusion pump (Flo-Guard 800™, Travenol Inc). Pigs randomized to an arm not exposed to LPS received Sham LPS (500 ml saline vehicle only).

Chemically Modified Tetracycline (CMT-3)

CMT-3 (6-demethyl-deoxy-4-dedimethylaminotetracycline) is dissolved in Dimethyl Sulfoxide, and then administered intravenously at a dose to achieve a 25 μM (9.2 μg/mL) blood concentration. We assumed predominantly intravascular distribution for our dosing regimine. This method of delivery only achieved a serum concentration of 1.2±0.367 μg/mL at one hour as determined by High Pressure Liquid Chromatography.

Calculations

Based on the collected data the following calculations were performed on the Baxter Explore™ cardiac output computer:

Venous admixture was calculated utilizing the following equation:

$$\text{Venous admixture } (Q_s/Q_t) = \frac{100 \cdot [(Hgb \cdot 1.38) + (0.0031 \cdot PAO_2) - CaO_2]}{[(Hgb \cdot 1.38) + (0.0031 \cdot PAO_2) - CvO_2]}$$

where $CaO_2$ and $CvO_2$ are arterial and venous blood oxygen content, $Q_s$ is venous admixture blood flow, $Q_t$ is total blood flow, and $PAO_2$ is the partial pressure of alveolar oxygen. $CaO_2$, $CvO_2$, and $PAO_2$ were calculated utilizing the following equations:

$CaO_2 = (0.0138 \cdot Hgb \cdot SaO_2) + 0.0031 \cdot PaO_2$;

$CvO_2 = (0.0138 \cdot Hgb \cdot SvO_2) + 0.0031 \cdot PvO_2$;

$PAO_2 = [(Pbar - PH2O) \cdot FiO_2] - PaCO_2 \cdot [FiO_2 + (1 - FiO_2) \div 0.8)]$ Arterial ($SaO_2$) and venous ($SvO_2$) saturation were measured with the OSM3. Ventilatory Efficiency Index (VEI) has been previously validated and was calculated with the formula:

$$VEI(\text{ml/kg/cm H}_2\text{O}) = \frac{5 \text{ ml/kg/min}}{(\Delta P \cdot Rf \cdot PaCO_2)/760}$$

where $\Delta P$=the difference between peak and end expiratory pressure (mmHg) and Rf=respiratory frequency. The VEI is described in units analogous to compliance and was calculated assuming that the rate of total $CO_2$ production was constant at 5 ml/kg/min, and $P_AO_2 = PaCO_2$. The index allowed comparison of respiratory status among animals whose airway pressures, respiratory rate, and $PaCO_2$ vary throughout the experiment.

Bronchioalveolar Lavage (BAL)

At necropsy the bronchus to the left lower lobe was cannulated, secured so that it was isolated from the remaining bronchial tree, and then injected with 60 ml of saline as 3 aliquots of 20 ml each. Each aliquot was injected briskly and then withdrawn slowly 3 times to obtain an optimal BAL specimen. The combined aliquots of BAL fluid were spun at 1000 g for 10 min to remove cells and the supernatant was frozen at (−70°) for subsequent chemical analysis.

Gelatinase Activity

The methods for purification of collagenase have been fully described elsewhere. Briefly, to 900 μl of BAL fluid, 100 μl of 1X collagenase buffer (Tris 0.50 mM+NaCl 0.2 M+5 mM Calcium chloride+0.02% Brij) was added. 70 μl of this mixture+10 μl of 1.0 mM Aminophenyl mercuric acetate+10 μl of SBTI (300 mg/ml) was incubated at room temperature for one hour. Next, 10 μl of radiolabeled (Tritium) Type I rat skin gelatin was added and incubated at 37° C. for 4 hours. Then 50 μl of cold gelatin (2 mg/ml) and 100 μl of 45% Trichloroacetic acid was added with the entire mixture cooled at 4° C. for 30 minutes. The reaction mixture was centrifuged at 13,000 g for 15 minutes and a 100 μl aliquot removed to determine the amount of radioactivity released into the supernatant by liquid scintillation counting. Gelatinase activity was determined as:

$$\% \text{ Gelatin lysed} = \frac{(DPM \text{ in } 100\ \mu l \text{ supernatant} - DPM \text{ of the blank})2.5}{(DPM \text{ in } 10\ \mu l \text{ substrate})}$$

10 μL of the substrate contained 10 μg of the gelatin. By multiplying lysis by the substrate concentration and dividing by the time of incubation, we were able to calculate the quantity of substrate degraded per milligram of protein per hour.

Elastase activity

Elastase activity was determined by incubating 100 μl of the BAL fluid and 400 μl of the 1.25 mM specific synthetic elastase substrate madhouse seconal-ala-ala-pro-val-p-nitroanilide in a 96-well ELISA plate at 37° C. for 18 hr. At the end of the incubation, the optical density was read at 405 mM. The data were expressed as η mol elastase substrate degraded per milligram of protein per hour. These methods are described in full detail elsewhere.

BAL Protein

BAL protein analysis was based on the Bradford protein assay (BioRad) with albumin as the standard. The standards ranged from 70 μ/ml to 1.40 mg/ml. 20 milliliters of Coomasie blue dye solution was diluted to 100 mL with saline. Either 100 μl of standard solution or 100 μl of BAL fluid was added to 5 ml of Coomasie blue solution and the optical density was read at 575 nm in a spectrophotometer. The results were reported as micrograms of protein per 100 μl of BAL fluids.

Neutrophil Infiltration

At necropsy the right middle lobe was excised and its bronchus cannulated. Glutaraldehyde fixative (2.5%, phosphate-buffered) was slowly instilled until air was no longer displaced from the bronchus. The lung was then immersed in glutaraldehyde and additional fixative was infused with a syringe until airway pressure of the fixative stabilized at 25 mmHg. The cannula was clamped and the lobe was stored in glutaraldehyde at room temperature for 24 hours. To assure an unbiased histological assessment a stratified random sampling method was utilized. One tissue block from the fixed lobe of each animal was randomly chosen and processed for routine paraffin sectioning. Ten serial sections (7 µm thick) were made, individually mounted, and numbered consecutively. A random selection of either odd or even sections were stained with hematoxylin and eosin for histologic assessment. On each of the five sections per animal, a randomly placed sampling probe, consisting of 10 equidistant sampling points each, was established along the vertical axis. This method avoided overlap of sampling probes between sections from the same animal. Each area was located with the vernier scales of the microscope stage and then viewed with 100× oil immersion using a high-resolution video camera. Areas featuring bronchi, connective tissue septa, or blood vessels other than capillaries were discarded by advancing the stage 0.5 mm along the vertical axis of the section. This process limited quantification of neutrophils to the alveoli and interstitium only. Total neutrophil count was obtained, in all focal planes, from a sampling area of 6400 $\mu m^2$.

Lung Water

Representative tissue samples from both lungs were sharply dissected free of nonparenchymal tissue with care to avoid contact with tissue to be used. Samples were then placed in a dish and weighed. The specimen was then dried in an oven at 65° C. for 24 hours and then weighed again. Lung water was expressed as a wet to dry weight ratio (W/D).

Figure 1:
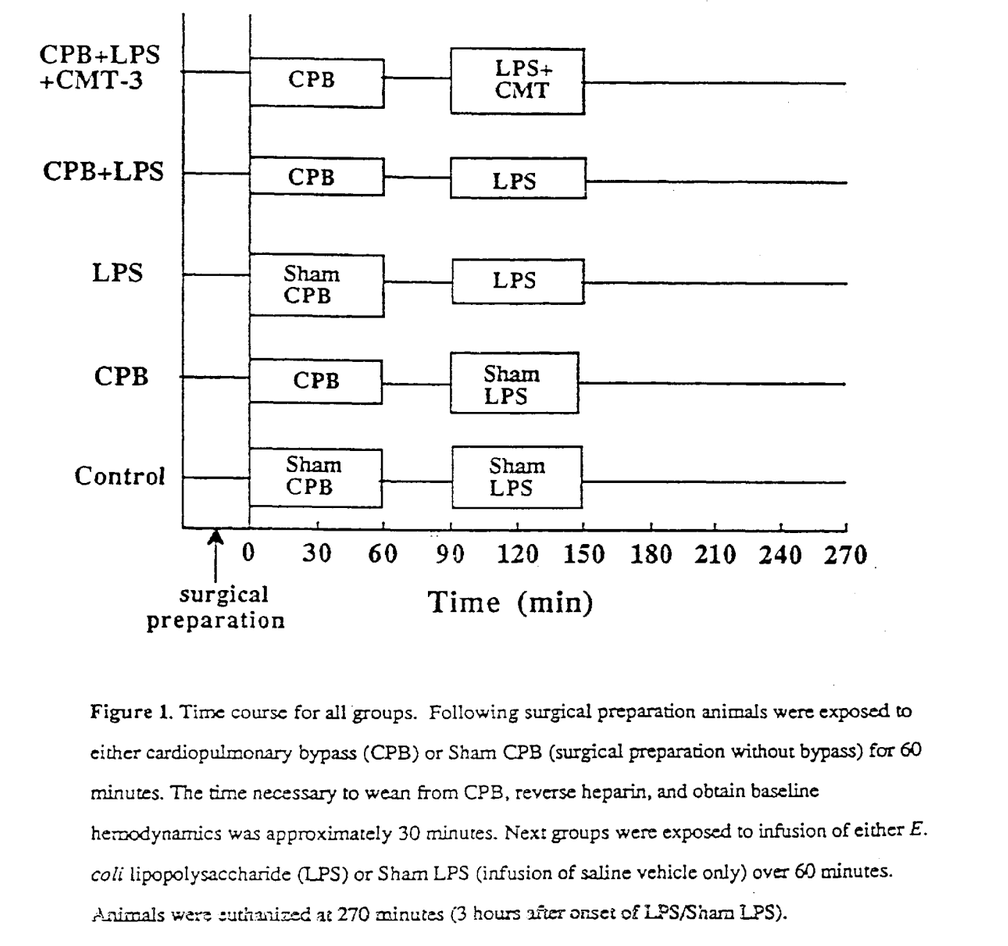
FIG. 1 is a graph showing the time course for all groups studied.

Protocol (see FIG. 1 for scheme)

Control: (n=3) Animals were subjected to 1 hour of Sham CPB (surgical preparation without bypass), followed by Sham LPS (infusion of saline vehicle without LPS) and then monitored for the 2 hours. Neither heparin nor protamine were given.

CPB: (n=4) Animals were subjected to 1 hour of CPB, followed by Sham LPS infusion and then monitored for 2 hours.

LPS: (n=6) Animals were subjected to 1 hour of Sham CPB followed by LPS infusion and monitored for 2 hrs. Neither heparin nor protamine were given.

CPB+LPS: (n=6) Animals were subjected to 1 hour of CPB followed by LPS infusion and monitored for 2 hrs.

CPB+LPS+CMT: (n=5) Animals were subjected to 1 hour of CPB followed by simultaneous infusion of LPS+CMT, and monitored for 2 hrs.

Statistics

Differences between physiologic parameters, neutrophil count, and protease activity were assessed using one-way analysis of variance with Newman-Keuls' post hoc analysis for between group comparisons and a repeat analysis of variance for within group comparisons. Mortality rate between groups was analyzed using Fischer's Exact Test. All evaluations employed a 95% confidence interval.

Animals

Animals were euthanized with an overdose of pentobarbital (90 mg/kg IV). The experiments described in this study were performed in adherence with the National Institutes of Health guidelines for the use of experimental animals in research. The protocol was approved by the Committee for the Humane Use of Animals at the SUNY Health Science Center, Syracuse, N.Y.

RESULTS

Figure 2:
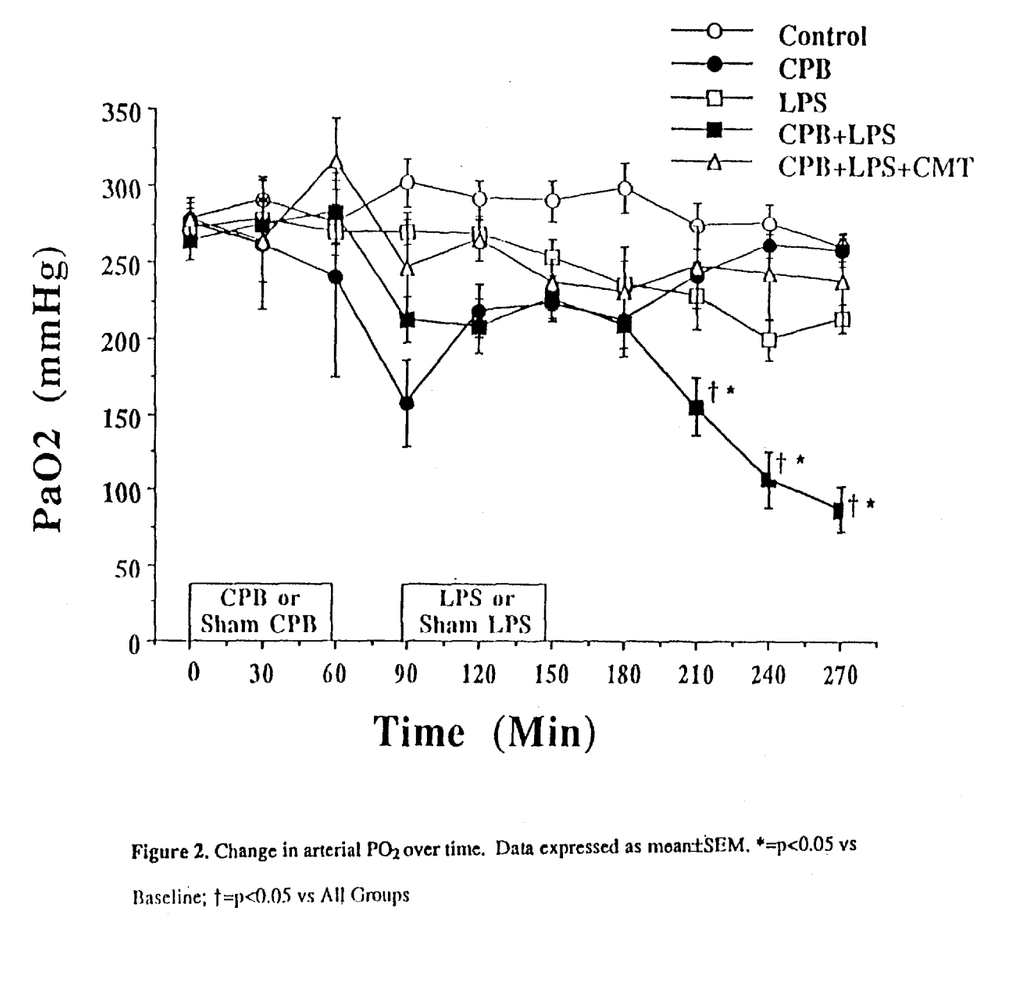
FIG. 2 is a graph showing the change in arterial $PO_2$ over time.
Figure 3:
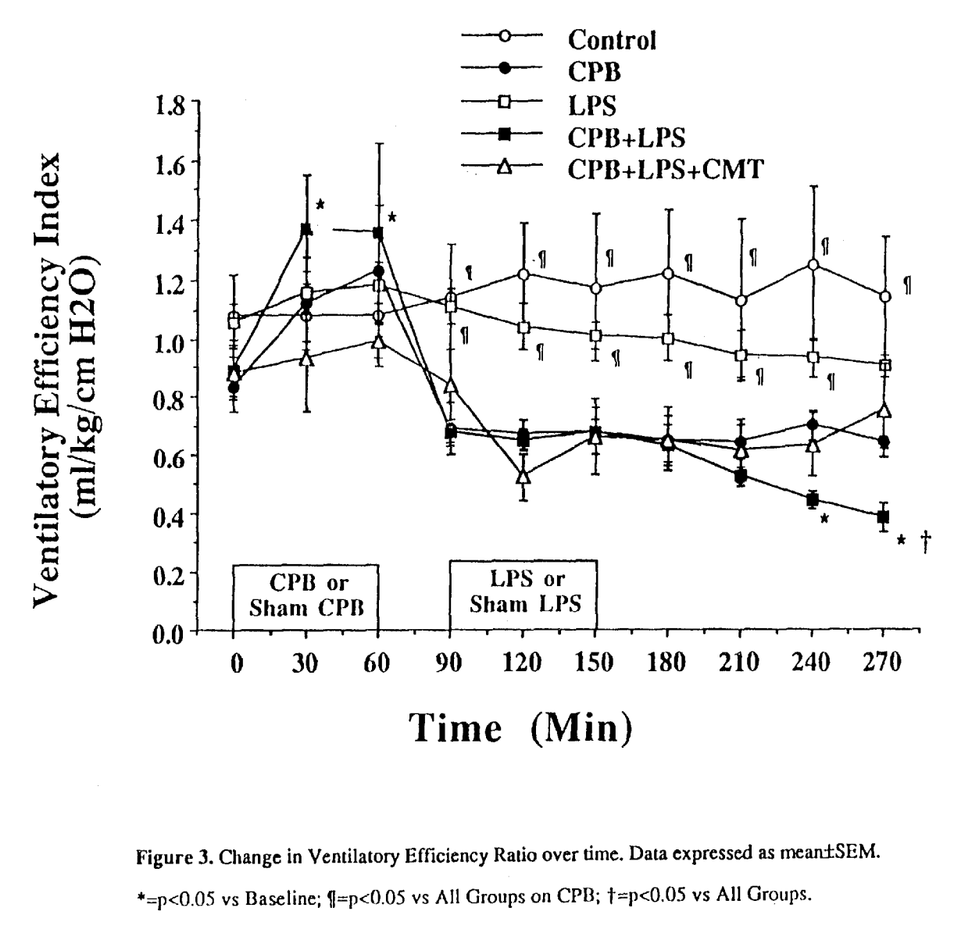
FIG. 3 is a graph showing change in ventilatory efficiency rate over time.
Figure 4:
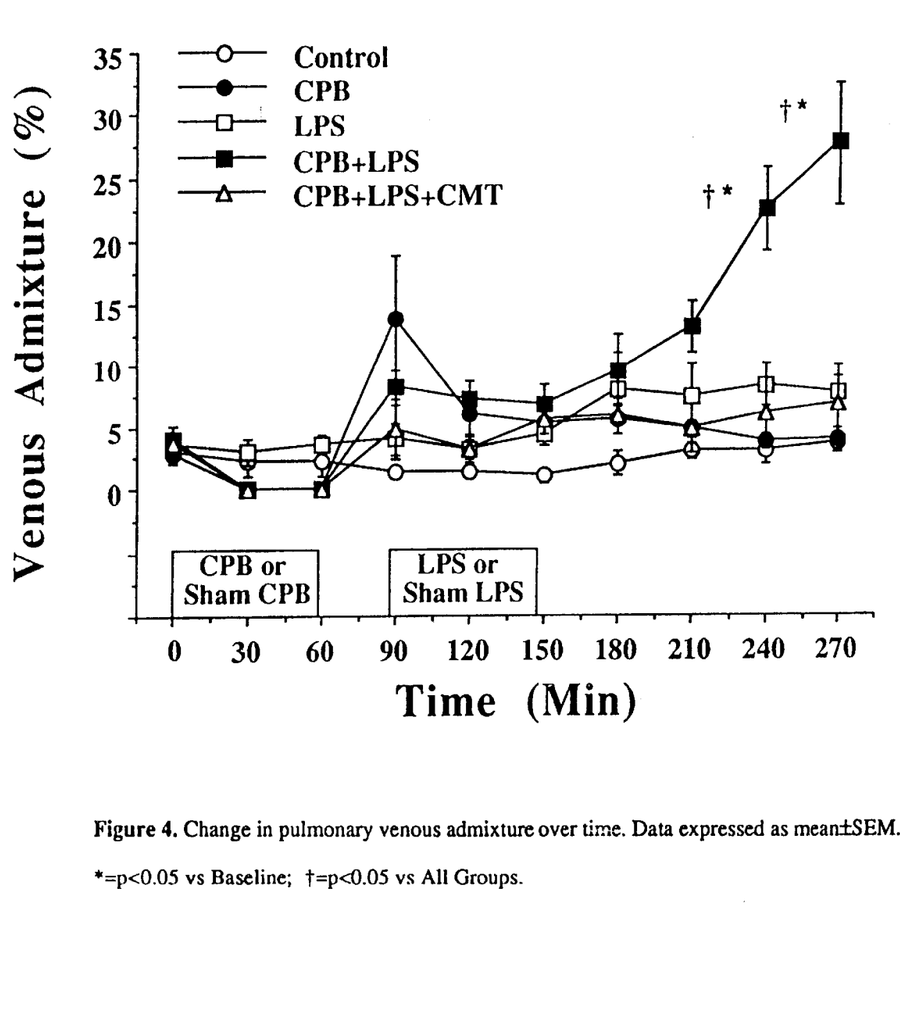
FIG. 4 is a graph showing the change in pulmonary venous admixture over time.
Figure 5:
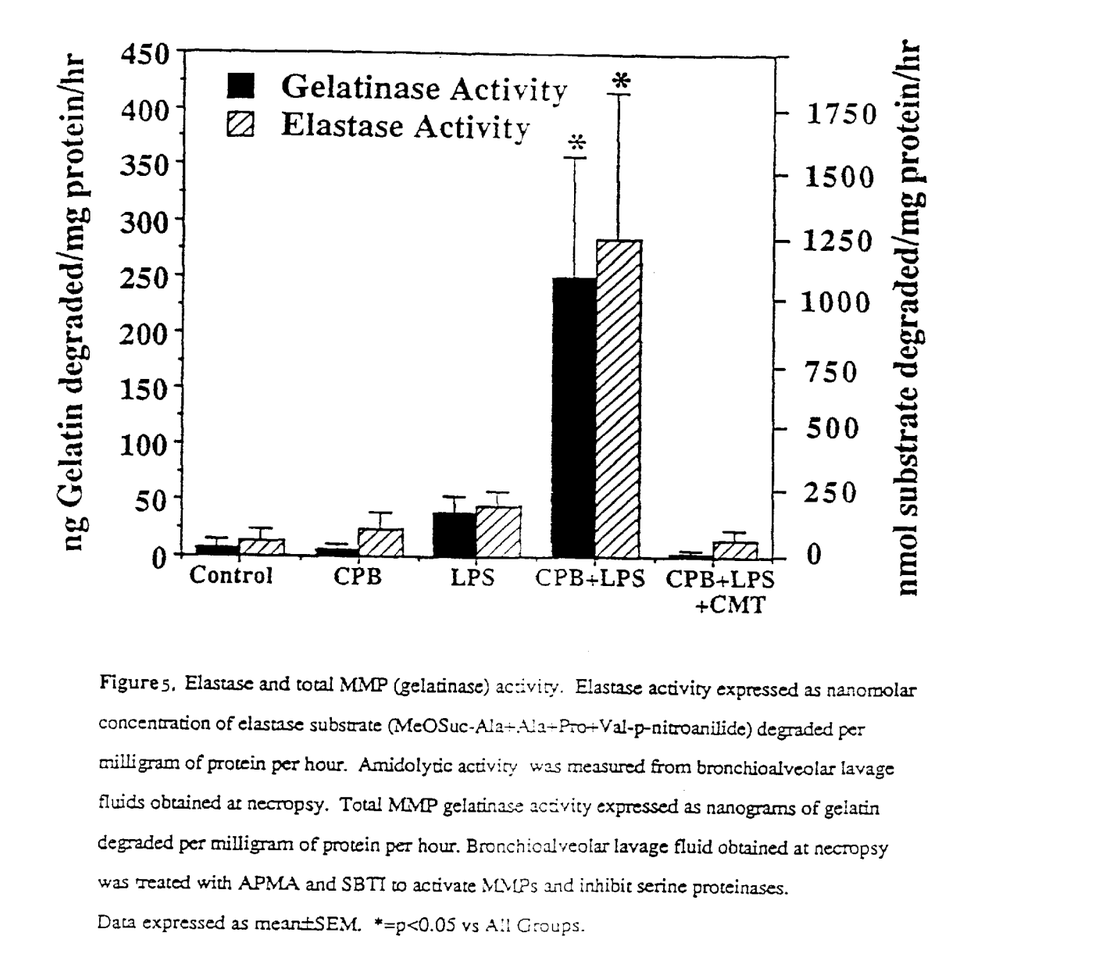
FIG. 5 is a graph showing the total elastase and MMP (gelatinase) activity.

CPB+LPS was the only group which developed severe physiologic lung injury typical of ARDS. Survival in this group was 60% at 270 minutes as compared to 100% in all other groups. Physiologically, this injury manifested as a significant fall in arterial oxygenation (FIG. 2), a fall in the Ventilatory Efficiency Index (FIG. 3), and an increase in venous admixture (FIG. 4). The VEI fell in all groups subjected to CPB. However, VEI improved in the group treated with CMT to remain significantly better than the CPB+LPS group at 270 minutes (FIG. 3). A similar trend was noted in the group exposed to CPB alone (FIG. 3). The drop in VEI in pigs exposed to CPB was due to an increase in $CO_2$ production requiring a significant increase in respiratory rate. The $CO_2$ production likely resulted from a conversion of bicarbonate and lactate which were used in the bypass circuit priming volume. There was a significant, progressive decrease in cardiac output over time in all groups. Cardiac output was significantly lower at 60 minutes in groups undergoing CPB because venous return limited pump flow to 2 L/min. All groups exposed to LPS developed a significant increase in pulmonary artery pressure by 150 minutes (Table 1). No significant change was noted in the Pulmonary Artery Occlusion Pressure for all groups.

Neutrophil infiltration into the pulmonary interstitium and alveoli was significantly greater (p<0.05) following CPB+ LPS (1.8±0.1 neutrophils per 6400 $\mu m^2$) as compared to Control (0.7±0.1), CPB (1.5±0.1), LPS (1.2±0.1) and CPB+ LPS+CMT (1.1±0.1). In addition, neutrophil infiltration following CMT treatment was significantly higher than Control levels (p<0.05), perhaps a result of initiating treatment one hour after CPB. Histologic sections from animals receiving either CPB or LPS were marked by thickened alveolar walls with greater leukocyte infiltration as compared to Controls. Animals exposed to both CPB+LPS exhibited more extensive leukocyte infiltration and congested blood vessels, compared to all other groups, which was ameliorated by treatment with CMT-3.

BAL analysis demonstrated a significant increase in elastase and gelatinase (FIG. 6) activity in the CPB+LPS group, as compared to all other groups. Both elastase and gelatinase activity were reduced to levels observed in Controls with CMT-3 treatment. Furthermore, total protein in BAL fluid increased significantly in animals exposed to LPS and increased still further with CPB+LPS (Table 2). However, treatment with CMT-3 ablated the increase in BAL protein seen in the CPB+LPS group (Table 2). Lung water, as determined by the W/D ratio, was highest in the CPB+LPS Group, but was not statistically different from all other groups (Table 2).

TABLE 1

Hemodynamic data over time.

|  | Time (min) | Cardiac Output (L/min) | PAP (mmHg) | PAOP (mmHg) |
|---|---|---|---|---|
| Control | 0 | 6.1 ± 0.4 | 18.7 ± 2.6 | 2.7 ± 1.2 |
| (n = 3) | 60 | 6.1 ± 1.1† | 18.7 ± 1.7 | 1.7 ± 0.3 |
|  | 150 | 2.6 ± 0.1* | 24.3 ± 1.5 | 2.7 ± 0.7 |
|  | 210 | 3.5 ± 0.3* | 26.7 ± 1.7 | 3.3 ± 0.7 |
|  | 270 | 3.1 ± 0.1* | 27.7 ± 1.8 | 5.0 ± 1.0 |
| CPB | 0 | 4.7 ± 0.7 | 18.2 ± 3.8 | 4.2 ± 1.5 |
| (n = 5) | 60 | 2.0 ± 0.1* | 28.0 ± 0.5 | 7.5 ± 1.2 |
|  | 150 | 3.5 ± 0.6 | 21.4 ± 4.3 | 5.4 ± 0.7 |
|  | 210 | 3.4 ± 0.6 | 23.6 ± 4.7 | 5.0 ± 0.3 |
|  | 270 | 3.7 ± 0.7 | 22.8 ± 3.5 | 6.0 ± 1.1 |
| LPS | 0 | 5.4 ± 0.4 | 18.7 ± 1.6 | 3.7 ± 0.3 |

TABLE 1-continued

Hemodynamic data over time.

|  | Time (min) | Cardiac Output (L/min) | PAP (mmHg) | PAOP (mmHg) |
|---|---|---|---|---|
| (n = 8) | 60 | 5.0 ± 0.6† | 23.3 ± 2.2 | 5.0 ± 1.2 |
|  | 150 | 2.8 ± 0.3* | 34.3 ± 2.9* | 6.1 ± 1.1 |
|  | 210 | 3.0 ± 0.2* | 35.0 ± 4.3*‡ | 5.3 ± 0.9 |
|  | 270 | 3.3 ± 0.4* | 37.0 ± 4.2*‡ | 6.9 ± 0.8 |
| CPB + LPS | 0 | 5.1 ± 0.6 | 15.5 ± 1.4 | 3.8 ± 0.6 |
| (n = 6) | 60 | 1.8 ± 0.1 | 26.0 ± 4.4 | 7.5 ± 2.4 |
|  | 150 | 3.7 ± 0.4 | 27.8 ± 2.0* | 6.3 ± 1.5 |
|  | 210 | 3.9 ± 0.2 | 32.8 ± 1.8*‡ | 5.5 ± 1.7 |
|  | 270 | 3.3 ± 0.2* | 40.7 ± 2.2*‡ | 7.5 ± 1.3 |
| CPB + LPS + | 0 | 5.4 ± 0.6 | 23.0 ± 3.2 | 3.6 ± 0.2 |
| CMT (n = 5) | 60 | 1.8 ± 0.1* | 17.8 ± 2.4 | 7.5 ± 2.4 |
|  | 150 | 2.7 ± 0.4 | 30.6 ± 4.0 | 4.4 ± 0.6 |
|  | 210 | 2.8 ± 0.3 | 34.4 ± 4.7 | 4.6 ± 0.7 |
|  | 270 | 2.2 ± 0.4* | 32.0 ± 5.2 | 7.4 ± 0.8 |

PAP = Pulmonary artery pressure, PAOP = Pulmonary artery occlusion pressure. See Methods for group description. Data are mean ± SEM. * = $p<0.05$ vs Baseline; ‡ = $p<0.05$ vs Control, CPB, and CPB + LPS; † = $p<0.05$ vs Control and LPS

TABLE 2

Total protein in bronchoalveolar lavage (BAL) fluid and total lung water at necropsy.

|  | Protein in BAL Fluid(ug/100 uL) | Lung Water (Wet/Dry Ratio) |
|---|---|---|
| Control | 20.3 ± 2.07 | 5.8 ± 0.3 |
| CPB | 19.0 ± 1.65 | 6.3 ± 1.2 |
| LPS | 24.9 ± 3.24* | 6.4 ± 0.5 |

TABLE 2-continued

Total protein in bronchoalveolar lavage (BAL) fluid and total lung water at necropsy.

|  | Protein in BAL Fluid(ug/100 uL) | Lung Water (Wet/Dry Ratio) |
|---|---|---|
| CPB + LPS | 32.3 ± 2.50* | 7.2 ± 0.3 |
| CPB + LPS + CMT | 17.2 ± 2.12 | 6.6 ± 0.6 |

Extracapillary preotein extravasation determined by protein analysis of BAL fluid obtained at necropsy. Protein quantification by biorad assay compared to albumin standard. Total lung water as determined by wet/dry ratio from representative specimens obtained at necropsy. * = $P<0.05$ vs Control, CPB, CPB + LPS + CMT.

We claim:

1. A method for preventing acute lung injury in a mammal following trauma, the method comprising treating the mammal with an effective amount of a tetracycline prior to significant intrapulmonary accumulation of neutrophils.

2. The method of claim 1 wherein the tetracycline has substantially no antibacterial activity.

3. The method of claim 1 wherein the tetracycline is 6-demethyl-6-deoxy-4-de(dimethylamino)tetracycline (CMT-3).

4. The method of claim 1 wherein the tetracycline is 4-de(dimethylamino)tetracycline (CMT-1).

5. The method of claim 1 wherein the tetracycline is 6-deoxy-5α-hydroxy-4-de(dimethylamino)tetracycline (CMT-8).

6. The method of claim 1 wherein the tetracycline is 4-de(dimethylamino)minocycline (CMT-10).

* * * * *

UNITED STATES PATENT AND TRADEMARK OFFICE
CERTIFICATE OF CORRECTION

PATENT NO. : 5,977,091
DATED : November 2, 1999
INVENTOR(S) : Nieman, et al.

It is certified that error appears in the above-identified patent and that said Letters Patent is hereby corrected as shown below:

Column 8, line 56, now reads "ranged from 70 µ/ml to 1.40 mg/ml."
should read -- ranged from 70 µg/ml to 1.40 mg/ml. --

Signed and Sealed this

Fifth Day of September, 2000

Attest:

Q. TODD DICKINSON

*Attesting Officer*          *Director of Patents and Trademarks*

UNITED STATES PATENT AND TRADEMARK OFFICE
CERTIFICATE OF CORRECTION

PATENT NO. : 5,977,091
DATED : November 2, 1999
INVENTOR(S) : Gary Nieman, et al.

It is certified that error appears in the above-identified patent and that said Letters Patent is hereby corrected as shown below:

Column 1, line 3:

insert --This work was suported by the following grants: DR14817 from Cystic Fibrosis Foundation; DEO3987 and DE10985 from the N.I.H. The government has certain rights to this invention.--

Signed and Sealed this

Twenty-sixth Day of December, 2000

Attest:

Q. TODD DICKINSON

Attesting Officer

Director of Patents and Trademarks

UNITED STATES PATENT AND TRADEMARK OFFICE
CERTIFICATE OF CORRECTION

PATENT NO.   : 5,977,091
DATED        : November 2, 1999
INVENTOR(S)  : Nieman et al.

It is certified that error appears in the above-identified patent and that said Letters Patent is hereby corrected as shown below:

<u>Column 1,</u>
Line 3, insert -- This invention was made with government support under Grant No. R41HL65030-01 awarded by the National Institutes of Health. The Government has certain rights in the invention. --

Signed and Sealed this

First Day of July, 2003

JAMES E. ROGAN
*Director of the United States Patent and Trademark Office*